US010940468B2

(12) United States Patent
Punji et al.

(10) Patent No.: US 10,940,468 B2
(45) Date of Patent: Mar. 9, 2021

(54) NICKEL CATALYST, PROCESS FOR PREPARATION AND USE THEREOF

(71) Applicant: Council of Scientific & Industrial Research, New Delhi (IN)

(72) Inventors: Benudhar Punji, Pune (IN); Vineeta Soni, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 173 days.

(21) Appl. No.: 16/083,085

(22) PCT Filed: Mar. 6, 2017

(86) PCT No.: PCT/IN2017/050082
§ 371 (c)(1),
(2) Date: Sep. 7, 2018

(87) PCT Pub. No.: WO2017/154022
PCT Pub. Date: Sep. 14, 2017

(65) Prior Publication Data
US 2019/0060889 A1 Feb. 28, 2019

(30) Foreign Application Priority Data
Mar. 8, 2016 (IN) .............................. 201611008016

(51) Int. Cl.
| | |
|---|---|
| B01J 31/18 | (2006.01) |
| C07F 15/04 | (2006.01) |
| C07D 401/04 | (2006.01) |
| C07D 403/04 | (2006.01) |
| C07B 37/02 | (2006.01) |
| C07D 209/04 | (2006.01) |

(52) U.S. Cl.
CPC .......... *B01J 31/183* (2013.01); *C07D 401/04* (2013.01); *C07D 403/04* (2013.01); *C07F 15/045* (2013.01); *B01J 2531/847* (2013.01); *C07B 37/02* (2013.01); *C07D 209/04* (2013.01)

(58) Field of Classification Search
None
See application file for complete search history.

(56) References Cited

PUBLICATIONS

Roquet, et al., "Catalytic Functionalization of C(sp$^2$)—H and C(sp$^3$)—H Bonds by Using Bidentate Directing Groups", Angewandte Chemie Int'l Edition, pp. 11726-11743, 2013.
Corbet et al., "8-Aminoquinoline: A Powerful Directing Group in Metal-Catalyzed Direct Functionalization of C—H Bonds", Angew. Chem. Int. Ed. Engl., vol. 52, No. 38, 2013, pp. 9896-9898.
Aihara et al., "Nickel-Catalyzed Direct Alkylation of C—H Bonds in Benzamides and Acrylamides with Functionalized Alkyl Halides via Bidentate-Chelation Assistance", Journal of the American Chemical Society, vol. 135, No. 14, pp. 5308-5311.
Tiwari et al., "Ruthenium-Catalyzed Heteroatom-Directed Regioselective C—H Arylation of Indoles Using a Removable Tether", Organic Letters, vol. 17, No. 7, 2015, pp. 1766-1769.
Punji et al., "Cobalt-Catalyzed C—H Bond Functionalizations with Aryl and Alkyl Chlorides", Chem. Eur. J., vol. 19, 2013, pp. 10605-10610.
Joucla et al., "Transition Metal-Catalysed, Direct and Site-Selective N1-, C2- or C3-Arylation of the Indole Nucleus: 20 Years of Improvements", Adv. Synth Catal., vol. 351, 2009, pp. 673-714.
Vechorkin et al., "The Nickel/Copper-Catalyzed Direct Alkylation of Heterocyclic C—H Bonds", Angewandte Chemie International Edition, vol. 49, No. 17, 2010, pp. 3061-3064.
Sandtorv, "Transition Metal-Catalyzed C—H Activation of Indoles", Adv. Synth. Catal., vol. 357, 2015, pp. 2403-2435.
Wang et al., "Rhodium-catalyzed regioselective direct C—H arylation of indoles with aryl boronic acids", Tetrahedron Letters, vol. 56, No. 24, 2015, pp. 3754-3757.
Yao et al., "Palladium- and Nickel-Catalyzed Direct Alkylation of Azoles with Unactivated Alkyl Bromides and Chlorides", Chemistry—A European Journal, vol. 16, No. 41, 2010, pp. 12307-12311.
Xin et al., "Nickel catalyzed alkylation of N-aromatic heterocycles with Grignard reagents through direct C—H bond functionalization", Chem. Commun., vol. 48, 2012, pp. 6717-6719.
Jiao et al., "Regioselective Direct C—H Alkylation of NH Indoles and Pyrroles by a Palladium/Norbornene-Cocatalyzed Process", Synthesis, vol. 46, No. 01, 2014, pp. 35-41.
Wu et al., "A General Palladium-Catalyzed Method for Alkylation of Heteroarenes Using Secondary and Tertiary Alkyl Halides", Angew Chem Int Ed Engl, vol. 53, No. 49, 2014, pp. 13573-13577.
Muto et al., "C—H arylation and alkenylation of imidazoles by nickel catalysis: solvent-accelerated imidazole C-H activation", Chemical Science, vol. 6, 2015, pp. 6792-6798.
Ackermann et al., "Ruthenium-Catalyzed Direct C—H Bond Arylations of Heteroarenes", Organic Letters, vol. 13, No. 13, 2011, pp. 3332-3335.
Song et al., "Nickel-Catalyzed C—H Alkylations: Direct Secondary Alkylations and Trifluoroethylations of Arenes", Angew. Chem. Int. Ed. Engl., vol. 53, No. 9, 2014, pp. 2477-2480.
Ackermann et al., "User-Friendly [Diglyme)NiBr2]-Catalyzed Direct Alkylations of Heteroarenes with Unactivated Alkyl Halides through C—H Bond Cleavages", Adv. Synth. Catal., vol. 353, 2011, pp. 3325-3329.
Wang et al., "Rh(III)-Catalyzed C—H Alkylation of Arenes Using Alkylboron Reagents", Organic Letters, vol. 17, No. 11, 2015, pp. 2812-2815.
Ackermann et al., "Metal-catalyzed direct alkylations of (hetero)arenes via C—H bond cleavages with unactivated alkyl halides", Chem. Commun., vol. 46, 2010, pp. 4866-4877.

(Continued)

*Primary Examiner* — Yun Qian
(74) *Attorney, Agent, or Firm* — Dinsmore & Shohl, LLP

(57) ABSTRACT

The present invention disclosed to a novel nickel catalyst of formula (I) process for preparation of the same and use of nickel catalyst of formula (I) for C—H bond alkylation, and benzylation of heteroarenes.

10 Claims, No Drawings

(56) References Cited

PUBLICATIONS

Soni et al., "Unified Strategy for Nickel-Catalyzed C-2 Alkylation of Indoles through Chelation Assistance", ACS Catalysis, vol. 6, No. 9, 2016, pp. 56666-5672.

International Search Report and Written Opinion completed Jun. 30, 2017, pertaining to PCT/IN2017/050082, filed Mar. 6, 2017.

NICKEL CATALYST, PROCESS FOR PREPARATION AND USE THEREOF

The following specification particularly describes the invention and the manner in which it is to be performed.

FIELD OF THE INVENTION

The present invention relates to a novel nickel catalyst of formula (I). More particularly, the present invention relates to a novel nickel catalyst of formula (I), process for preparation of the same and use of nickel catalyst of formula (I) for C—H bond alkylation or benzylation of heteroarenes.

BACKGROUND AND PRIOR ART

Heteroarenes are the very important building blocks in many pharmaceutically relevant compounds and biologically active natural products; hence the efficient and regioselective functionalization of heteroarenes like, indoles, pyrazoles and imidazoles are highly desirable. Indoles are indispensable substructures of various natural products, drugs, and biologically active compounds. Thus, there is a growing interest in the efficient and selective functionalization of indoles, particularly by developing the strategies based on transition-metal-catalyzed direct C—H bond activation. While various effective methods were devised for the regioselective arylations and alkenylations of indoles, significantly more challenging C—H bond alkylation with unactivated alkyl halides containing β-hydrogen is very scarce, which is mainly due to the difficulty in oxidative addition of alkyl halides onto the transition metals and their tendency to β-hydride eliminations. Indeed, only a few methods for direct alkylation of indoles with alkyl halides have been reported with a precious Pd-metal catalyst. In light of the beneficial features of earth-abundant 3d transition metals, Ackermann et al. described an inexpensive co-catalyzed C-2 alkylation of indoles with primary alkyl chlorides. However, the use of a strong base, the Grignard reagent CyMgCl, is the major limitation associated with this method. A variety of nickel-catalyzed C—H functionalization have been established and found beneficial for organic synthesis. In general, Ni-catalyzed regioselective C—H functionalization has thus far been limited, with few exceptions, to the (hetero)arenes containing a N,N-bidentate auxiliary, (quinolin-8-yl)amide or (pyridin-2-yl)isopropyl amide. Along those lines, Ackermann et al. reported a Ni-catalyzed alkylation of indole-3-carboxamide with secondary alkyl halides through bidentate-chelate assistance, only with a limited scope. The bidentate directing group largely binds the Ni center more tightly and lowers the C—H activation barrier to facilitate the (hetero)arene C—H installation of an expensive bidentate auxiliary on each substrate before the C—H functionalization, which are the major disadvantages associated with it.

The regioselective direct C—H arylation and alkenylation at either the C2- or C3-position of indole have been successfully achieved by using palladium, rhodium, or copper catalysis. However, attempts to perform direct C—H alkylation reactions of indoles have been less successful so far. Although the 3-alkylation of indole can be achieved by catalytic methods such as Friedel-Crafts alkylation, allylic alkylation, and conjugate addition. A general protocol for the regioselective direct C—H alkylation at the C2-position of free N—H indoles has not yet been established. Given the limited availability of synthetic routes toward 2-alkylindoles, a straight-forward approach is highly demanded.

Article titled "8-Aminoquinoline: A Powerful Directing Group in Metal-Catalyzed Direct Functionalization of C—H Bonds" by M Corbet et al. published in *Angew Chem Int Ed Engl.*, 2013 ;52(38); pp 9896-9898 reports the 8-aminoquilonine auxiliary has recently gained much attention because of its versatility as a directing group in many metal-catalyzed direct CH bond functionalizations. Its chelating ability, its rigid backbone, and relatively acidic NH bond have proven to be critical in most transformations.

Article titled "Nickel-Catalyzed Direct Alkylation of C—H Bonds in Benzamides and Acrylamides with Functionalized Alkyl Halides via Bidentate-Chelation Assistance" by Y Aihara published in *J. Am. Chem. Soc.,* 2013, 135 (14), pp 5308-5311 reports the alkylation of the ortho C—H bonds in benzamides and acrylamides containing an 8-aminoquinoline moiety as a bidentate directing group with unactivated alkyl halides using nickel complexes as catalysts.

Article titled "Ruthenium-Catalyzed Heteroatom-Directed Regioselective C—H Arylation of Indoles Using a Removable Tether" by V K Tiwari et al. published in Org. Lett., 2015, 17 (7), pp 1766-1769 reports a new approach to C-2 arylated indoles has been developed by utilizing a ruthenium-catalyzed, heteroatom-directed regioselective C—H arylation. The reaction is highly site-selective and results in very good yields.

Article titled "Cobalt-Catalyzed C—H Bond Functionalizations with Aryl and Alkyl Chloride" by B Punji et al. published in *Chem. Eur. J.,* 2013, 19, pp 10605-10610 reports. Inexpensive cobalt catalysts derived from N-heterocylic carbenes (NHC) allowed efficient catalytic C—H bond arylations on heteroaryl-substituted arenes with widely available aryl chlorides, which set the stage for the preparation of sterically hindered tri-ortho-substituted biaryls. The cobalt-catalyzed C—H bond functionalizations occurred efficiently at ambient reaction temperature with excellent levels of site-selectivities and ample scope.

Review article titled "Transition Metal-Catalysed, Direct and Site-Selective N1-, C2- or C3-Arylation of the Indole Nucleus: 20 Years of Improvements" by L Joucla et. al. published in *Adv. Synth. Catal.,* 2009, 351, pp 673-714 reports a review of transition Metal-Catalysed, Direct and Site-Selective N1-, C2- or C3-Arylation of the Indoles.

Article titled "The Nickel/Copper-Catalyzed Direct Alkylation of Heterocyclic C—H Bonds" by 0 Vechorkin et al. published in *Angewandte Chemie International Edition,* 2010, 49 (17), pages 3061-3064 reports a general and straightforward protocol for the cross-coupling of non-activated alkyl halides with heterocyclic C—H bonds. The method employs cheap nickel/copper catalysts, and expands significantly the scope of C—H functionalization.

Article titled "Transition Metal-Catalyzed C—H Activation of Indoles" by AH Sandtory et al. published in *Adv. Synth. Catal.,* 2015, 357, pp 2403-2435 discusses recent advances and strategies for transition metal-catalyzed C—H activation of indoles.

Article titled "Rhodium-catalyzed regioselective direct C—H arylation of indoles with aryl boronic acids" by L Wang et al. published in *Tetrahedron Letters,* 2015, 56 (24), pp 3754-3757 reports a highly efficient Rh(III)-catalyzed direct C—H arylation of indoles with aryl boronic acids under mild conditions. The methodology features wide substrate scope and excellent functional group compatibility (34 examples, up to 99% yield). The arylated products can also be conveniently transformed into biologically active polycyclic indole derivatives.

Article titled "Palladium- and nickel-catalyzed direct alkylation of azoles with unactivated alkyl bromides and chlorides" by T Yao et al. published in *Chemistry—A European Journal*, 2010, 16 (41), pp 12307-12311 reports the catalytic direct C[BOND]H alkylation of azoles with unactivated alkyl bromides and chlorides. A palladium catalyst enables the alkylation of oxazoles, whereas a nickel one shows unique activity for thiazole. The catalyses allow a straightforward access to azole motifs bearing long, functional alkyl side chains.

Article titled "Nickel catalyzed alkylation of N-aromatic heterocycles with Grignard reagents through direct C—H bond functionalization" by PY Xin et al. published in *Chem. Commun.*, 2012,48, 6717-6719 reports a novel protocol for nickel-catalyzed direct $sp^2$ C—H bond alkylation of N-aromatic heterocycles. This new reaction proceeded efficiently at room temperature using a Grignard reagent as the coupling partner.

Article titled "Regioselective Direct C—H Alkylation of NH Indoles and Pyrroles by a Palladium/Norbornene-Cocatalyzed Process" by L Jiao et al. published in *Synthesis;* 2014; 46(01); pp 35-41 reports nitrogen-containing heterocycles, including 1H-indoles and electron-deficient 1H-pyrroles, undergo a palladium/norbornene-cocatalyzed regioselective alkylation at the C—H bond adjacent to the NH group. A primary alkyl halide is used as the electrophile and the reaction proceeds smoothly under mild conditions to give 2-alkyl-1H-indoles and 2-substituted or 2,3-disubstituted 5-alkyl-1H-pyrroles in good yields.

Article titled "A General Palladium-Catalyzed Method for Alkylation of Heteroarenes Using Secondary and Tertiary Alkyl Halides" by X Wu et al. published in *Angew Chem Int Ed Engl;*2014; 53 (49); pp 13573-13577 reports a general alkylation of heterocycles using a simple palladium catalyst. Most classes of heterocycles, including indoles and pyridines, efficiently coupled with unactivated secondary and tertiary alkyl halides. An alkyl radical addition to neutral heteroarenes.

Article titled "C—H arylation and alkenylation of imidazoles by nickel catalysis: solvent-accelerated imidazole C—H activation" by K Muto et al. published in *Chem. Sci.*, 2015,6, 6792-6798 reports the first nickel-catalyzed C—H arylations and alkenylations of imidazoles with phenol and enol derivatives. Under the influence of $Ni(OTf)_2$/dcype/ $K_3PO_4$ (dcype: 1,2-bis(dicyclohexylphosphino)ethane) in t-amyl alcohol, imidazoles can undergo C—H arylation with phenol derivatives. The C—H arylation of imidazoles with chloroarenes as well as that of thiazoles and oxazoles with phenol derivatives can also be achieved with this catalytic system.

Article titled "Ruthenium-Catalyzed Direct C—H Bond Arylations of Heteroarenes" by L Ackermann et al. published in *Org. Lett.*, 2011, 13 (13), pp 3332-3335 reports Ruthenium-catalyzed C—H bond arylations of indoles, thiophenes, and pyrroles were accomplished in a highly chemo- and site-selective manner through the use of removable directing groups.

Article titled "Nickel-catalyzed C—H alkylations: direct secondary alkylations and trifluoroethylations of arenes" by W Song et al. published in *Angew Chem Int Ed Engl.;* 2014; 53(9); pp 2477-2480 reports a versatile nickel catalyst allowed for C—H alkylations of unactivated arenes with challenging secondary alkyl bromides and chlorides. The high catalytic efficacy also set the stage for direct secondary alkylations of indoles as well as C—H trifluoroethylations with ample substrate scope.

Article titled "User-Friendly [(Diglyme)NiBr$_2$]-Catalyzed Direct Alkylations of Heteroarenes with Unactivated Alkyl Halides through C—H Bond Cleavages" L Ackermann et al. published in *Adv. Synth. Catal.;* 2011, 353, pp 3325-3329 reports reports a nitrogen and phosphorus ligand-free catalytic system derived from inexpensive [(diglyme) NiBr$_2$] allowed for efficient direct C—H bond alkylations of heteroarenes with unactivated β-hydrogen-containing alkyl halides under basic reaction conditions.

Article titled "Rh(III)-Catalyzed C—H Alkylation of Arenes Using Alkylboron Reagents" by H Wang et al. published in *Org. Lett.*, 2015, 17 (11), pp 2812-2815 reports Rhodium(III)-catalyzed direct alkylation of arenes using commercially available alkyltrifluoroborates. Oximes, heteroarenes, azomethines, N-nitrosoamines, and amides are viable directing groups to entail this transformation. The alkyl group in the boron reagent can be extended to primary alkyls, benzyl, and cycloalkyls, and the reaction proceeded with controllable mono- and dialkylation selectivity when both ortho C—H sites are accessible.

Article titled "Transition Metal-Catalysed, Direct and Site-Selective N1-, C2- or C3-Arylation of the Indole Nucleus: 20 Years of Improvements" by L Joucla et al. published in *Advanced Synthesis*, 2009, 351 (5), pp.673-714 reports the direct and site-selective transition metal-catalysed N1-, C2- or C3-arylations of indoles have been the subject of almost continuous improvements.

Article titled "Metal-catalyzed direct alkylations of (hetero)arenes via C—H bond cleavages with unactivated alkyl halides " by L Ackermann et al. published in *Chem. Commun.*, 2010,46, pp 4866-4877 reports a valuable asset of these methodologies is represented by their excellent regio- and chemoselectivities, along with remarkable mild reaction conditions, rendering this approach an attractive alternative to traditional alkylation strategies.

The prior art reports expensive catalysts such as palladium and rhodium for selective C—H bond alkylation, benzylation and arylation of these heteroarenes. These noble metal catalysts are very expensive because of the scarcity of these metal precursors in earth-crust. Further, the reported benzylation process of indoles via C(sp2)-H/C(sp3)-H oxidative coupling with toluene derivatives uses strong oxidants, such as peroxides or secondary transition-metal.

Therefore there is need in the art to develop an inexpensive nickel (earth-abundant) catalyst system which performs the alkylation and benzylation of various heteroarenes under mild reaction conditions.

OBJECTIVE OF INVENTION

The main objective of the present invention is to provide a nickel catalyst of formula (I) and process for preparation thereof.

Another objective of the present invention is to provide a process for the alkylation or benzylation—of heteroarenes with selectively at C2 position.

SUMMARY OF THE INVENTION

Accordingly, the present invention provides a novel nickel catalyst of formula (I);

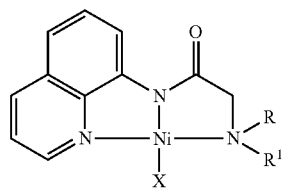

Formula I

Wherein;

R and R¹ are the same and are selected from the group consisting of alkyl, aryl, benzyl, heteroaryl, —(CH$_2$)$_2$O (CH$_2$)$_2$—, —(CH$_2$)$_2$N(Me)(CH$_2$)$_2$—, —(CH$_2$)$_4$—, —(CH$_2$)$_5$—, etc. X is selected from the group consisting of hydrogen, halogen, OC(O)CH$_3$, OC(O)$^t$Bu, OC(O)Ph, OC(O)admantyl, OSO$_2$CF$_3$, BF$_4$, SbF$_6$, etc.

In preferred embodiment, said nickel catalyst of formula (I) is selected from ($^{R2}$NNN$^{8\text{-}Quin}$)-H, [2- (diethylamino)-N-(quinolin-8-yl)acetamide]($^{Et2}$NNN$^{8\text{-}Quin}$)NiCl, [2-(diethylamino)-N-(quinolin-8-yl) acetamide] (NiCl) ($^{Et2}$NNN$^{8\text{-}Quin}$) Ni(OAc), [2-(diethylamino)-N-(quinolin-8-yl) acetamide] Ni(OAc).

In another embodiment, the present invention provides a process for the preparation of nickel catalyst of formula (I), wherein said process comprising the steps of:
a) Refluxing the reaction mixture of 2-bromo-N-(quinolin-8-yl) acetamide and amino compound in solvent for the period ranging from 20 to 24 hrs at temperature ranging from 60 to 80° C. afford ($^{R2}$NNN$^{8\text{-}Quin}$)-H Ligands;
b) Adding triethylamine to the mixture of compound of step (a), nickel compound and solvent followed by refluxing the reaction mixture for the period in the range of 3 to 12 hrs at a temperature ranging from 60 to 70° C. to afford compound of formula (I).

In preferred embodiment, said amino compound is selected from diisopropyl amine, diethylamine, dimethyl amine, morpholine, N-methyl piperazine, cyclopentyl amine, cyclohexyl amine.

In another preferred embodiment, said nickel compound is selected from (DME)NiCl$_2$, (THF)NiBr$_2$, Ni(OAc)$_2$.

In yet another preferred embodiment, said solvent in step (a) and (b) is selected from Acetone or Tetrahydrofuran (THF).

In yet another embodiment, the present invention provides a process for the alkylation or benzylation of heteroarene in presence of novel nickel catalyst of formula (I), comprising stirring the reaction mixture of heteroarene, organic halide compound or benzyl compound, catalyst of formula (I), base and solvent at temperature ranging from 120 to 160° C. for the period ranging from 6 to 36 hrs to afford desired compound of formula (II).

In preferred embodiment, said heteroarene is selected from 1-(pyridine-2-yl)-1H-indole, 5-methyl-1-(pyridine-2-yl)-1H-indole, 5-methoxy-1-(pyridine-2-yl)-1H-indole, 5-fluoro-1-(pyridin-2-yl)-1H-indole, 5-bromo-1-(pyridine-2-yl)-1H-indole, 1-(pyridin-2-yl)-1H-indole-5-carbonitrile, 3-methyl-1-(pyridine-2-yl)-1H-indole, 1-(pyrimidin-2-yl)-1H-indole or 5-methoxy-1-(pyrimidin-2-yl)-1H-indole.

In another preferred embodiment, said organic halide compound is selected from 1-iodobutane, 1-iodopentane, 1-bromohexane, 1-bromodecane, 1-iodododecane, 1-bromotridecane, 1-bromotetradecane, 1-bromohexadecane, 1-bromooctadecane, 1-bromo-2-methylpropane, 1-bromo-3-methylbutane, (bromomethyl)cyclohexane, (2-bromoethyl)cyclohexane, 1-bromo-2,2-dimethylpropane, (3-bromopropyl)benzene, 1-(3-bromopropyl)-4-methoxybenzene, 1-chloro-4-iodobutane, 5-bromopent-1-ene, 9-(4-iodobutyl)-8a,9a-dihydro-9H-carbazole, 2-iodopropane, (1-bromoethyl)benzene, (bromoethylene)dibenzene, 2-iodobutane, bromocyclopropane, iodocyclopentane, bromocyclohexane, bromocycloheptane or 6-bromo-1-hexene.

In yet another preferred embodiment, said base is selected from Lithium bis(trimethylsilyl)amide [LiHMDS], Lithium tert-butoxide (LiOtBu) or mixture thereof.

In still another preferred embodiment, said benzyl compound is selected from toluene, p-xylene, m-xylene, 1-methoxy-4-methylbenzene, 1-fluoro-4-methylbenzene, 1-chloro-4-methylbenzene, 1-bromo-4-methylbenzene, ortho-xylene, 1-fluoro-2-methylbenzene, 1-chloro-2-methylbenzene, 1-bromo-2-methylbenzene, 1-methyl-2-(trifluoromethyl)benzene, mesitylene, 2,4-difluoro-1-methylbenzene, 1-methylnaphthalene, 1-(p-tolyl)-1H-indoletoluene.

In yet still another preferred embodiment, said solvent is selected from toluene, chlorobenzene or mixture thereof.

DETAILED DESCRIPTION OF THE INVENTION

The invention will now be described in detail in connection with certain preferred and optional embodiments, so that various aspects thereof may be more fully understood and appreciated.

In the view of above, the present invention provides a novel nickel catalyst of formula (I), process for preparation of the same and use of these nickel catalyst of formula (I) for C—H bond alkylation and, benzylation of heteroarenes.

In an embodiment, the present invention provides novel nickel catalyst of formula (I);

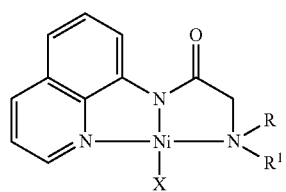

Formula I

Wherein;

R and R¹ are the same and are selected from the group consisting of alkyl, aryl, benzyl, heteroaryl, —(CH$_2$)$_2$O (CH$_2$)$_2$—, —(CH$_2$)$_2$N(Me)(CH$_2$)$_2$—, —(CH$_2$)$_4$—, —(CH$_2$)$_5$—, etc. X is selected from the group consisting of hydrogen, halogen, OC(O)CH$_3$, OC(O)$^t$Bu, OC(O)Ph, OC(O)admantyl, OSO$_2$CF$_3$, BF$_4$, SbF$_6$, etc.

In preferred embodiment, said nickel catalyst of formula (I) is selected from ($^{R2}$NNN$^{8\text{-}Quin}$)-H, [2-(diethylamino)-N-(quinolin-8-yl)acetamide] ($^{Et2}$NNN$^{8\text{-}Quin}$)NiCl [2-(diethylamine)-N-(quinolin-8-yl)acetamide](NiCl), ($^{Et2}$NNN$^{8\text{-}Quin}$) Ni(OAc) [2-(diethylamino)-N-(quinolin-8-yl)acetamide].

In another embodiment, the present invention provides a process for the preparation of nickel catalyst of formula (I), wherein said process comprising the steps of:

a) Refluxing the reaction mixture of 2-bromo-N-(quinolin-8-yl) acetamide and amino compound in solvent for the period ranging from 20 to 24 hrs at temperature ranging from 60 to 80° C. afford ($^{R2}$NNN$^{8-Quin}$)-H Ligands;

b) Adding triethylamine to the mixture of compound of step (a), nickel compound and solvent followed by refluxing the reaction mixture for the period in the range of 3 to 12 hrs at a temperature ranging from 60 to 70° C. to afford compound of formula (I).

In preferred embodiment, said amino compound is selected from diisopropyl amine, diethylamine, dimethyl amine, morpholine, N-methyl piperazine, cyclopentyl amine, cyclohexyl amine.

In another preferred embodiment, said nickel compound is selected from (DME)NiCl$_2$, (THF)NiBr$_2$, Ni(OAc)$_2$.

In yet another preferred embodiment said solvent in step (a) and (b) is selected from Acetone or Tetrahydrofuran (THF).

In yet another embodiment, the present invention provides a process for the alkylation or benzylation of heteroarene in presence of novel catalyst of formula (I), comprising stirring the reaction mixture of heteroarene, organic halide compound or benzyl compound, catalyst of formula (I), base and solvent at temperature ranging from 120 to 160° C. for the period ranging from 6 to 36 hrs to afford desired compound of formula (II).

In preferred embodiment, said heteroarene is selected from 1-(pyridine-2-yl)-1H-indole, 5-methyl-1-(pyridine-2-yl)-1H-indole, 5-methoxy-1-(pyridine-2-yl)-1H-indole, 5-fluoro-1-(pyridin-2-yl)-1H-indole, 5-bromo-1-(pyridine-2-yl)-1H-indole, 1-(pyridin-2-yl)-1H-indole-5-carbonitrile, 3-methyl-1-(pyridine-2-yl)-1H-indole, 1-(pyrimidin-2-yl)-1H-indole, 5-methoxy-1-(pyrimidin-2-yl)-1H-indole.

In another preferred embodiment, said organic halide compound is selected from 1-iodobutane, 1-iodopentane, 1-bromohexane, 1-bromodecane, 1-iodododecane, 1-bromotridecane, 1-bromotetradecane, 1-bromohexadecane, 1-bromooctadecane, 1-bromo-2-methylpropane, 1-bromo-3-methylbutane, (bromomethyl)cyclohexane, (2-bromoethyl)cyclohexane, 1-bromo-2,2-dimethylpropane, (3-bromopropyl)benzene, 1-(3-bromopropyl)-4-methoxybenzene, 1-chloro-4-iodobutane, 5-bromopent-1-ene, 9-(4-iodobutyl)-8a,9a-dihydro-9H-carbazole, 2-iodopropane, (1-bromoethyl)benzene, (bromoethylene)dibenzene, 2-iodobutane, bromocyclopropane, iodocyclopentane, bromocyclohexane, bromocycloheptane, 6-bromo-1-hexene.

In yet another preferred embodiment, said base is selected from Lithium bis(trimethylsilyl)amide [LiHMDS], Lithium tert-butoxide (LiOtBu) or mixture thereof.

In still another preferred embodiment, said benzyl compound is selected from toluene, p-xylene, m-xylene, 1-methoxy-4-methylbenzene, 1-fluoro-4-methylbenzene, 1-chloro-4-methylbenzene, 1-bromo-4-methylbenzene, ortho-xylene, 1-fluoro-2-methylbenzene, 1-chloro-2-methylbenzene, 1-bromo-2-methylbenzene, 1-methyl-2-(trifluoromethyl)benzene, mesitylene, 2,4-difluoro-1-methylbenzene, 1-methylnaphthalene, 1-(p-tolyl)-1H-indoletoluene.

In yet still another preferred embodiment, said solvent is selected from toluene, chlorobenzene or mixture thereof.

The process for the alkylation of heteroarenes is as shown in scheme 1:

Scheme: 1

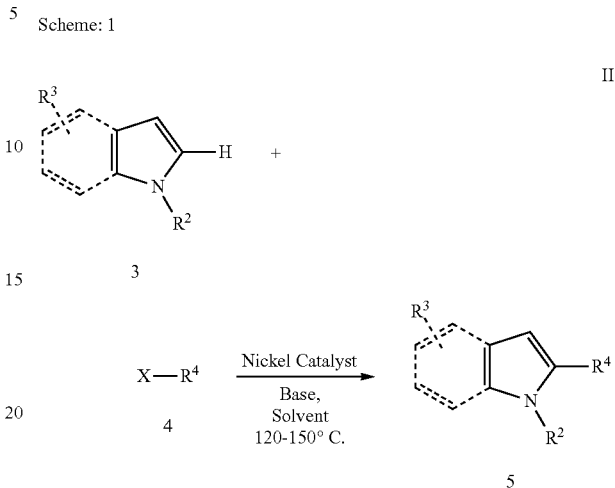

Wherein,

X is halogen selected from chlorine, bromine, iodine.

R$^2$ is selected from 2-pyridine, 2-pyrimidine, 2,4-pyrazine, etc.

R$^3$ is selected from hydrogen, alkyl, alkoxy, substituted alkoxy, phenoxy, halogens, trifluoromethyl, etc.

R$^4$ is selected from octyl, butyl, decyl, dodecyl, tetradecyl and others alkyl group The process for the benzylation of heteroarenes is as shown in scheme 2:

Scheme: 2

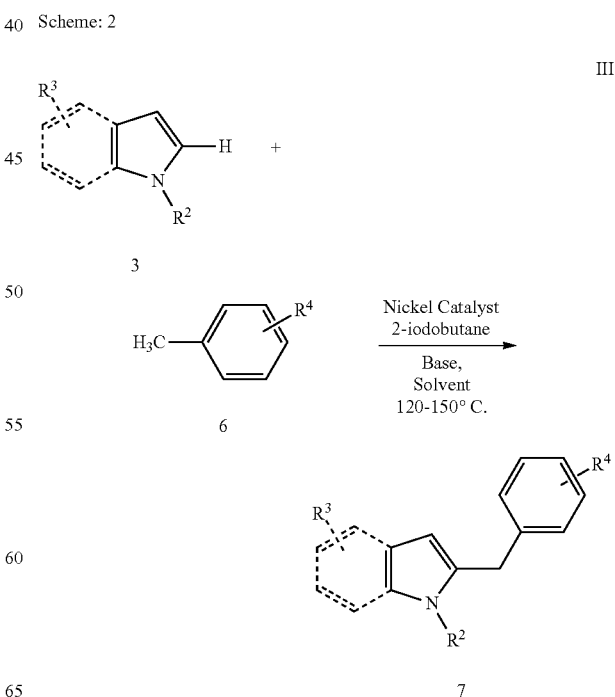

Wherein,

R² is selected from 2-pyridine, 2-pyrimidine, 2,4-pyrazine, 2-oxazole, etc.

R³ is selected from hydrogen, alkyl, alkoxy, substituted alkoxy, phenoxy, halogens, trifluoromethyl, etc.

R⁴ is selected from hydrogen, methyl, alkoxy, etc.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Synthesis of
2-Bromo-N-(Quinolin-8-yl)Acetamide

To a solution of 8-aminoquinoline (1.0 g, 6.94 mmol) in $CH_2Cl_2$ (40 mL), $Et_3N$ (1.02 mL, 7.32 mmol) was added at 0° C. and stirred for 20 min. To the resulted reaction mixture, bromo acetyl chloride (1.20 g, 7.64 mmol) was added dropwise via a syringe. The reaction mixture was then allowed to warm to room temperature and continued stirring for 24 h. At ambient temperature, the reaction mixture was quenched with water (20 mL) and extracted with $CH_2Cl_2$ (15 mL×3). The combined organic phase was washed with $H_2O$ (15 mL×3) and dried over $Na_2SO_4$. After filtration and evaporation of the solvents in vacuo, the crude product was purified by column chromatography on silica gel (n-hexane/EtOAc: 5/1) yielded the desired product as light yellow solid. Yield: 1.30 g (71%). $^1$H-NMR (400 MHz, CDCl$_3$): δ=10.89 (br s, 1H, N—H), 8.85 (dd, J=4.2, 1.5 Hz, 1H, Ar—H), 8.74 (dd, J=6.1, 2.9 Hz, 1H, Ar—H), 8.17 (dd, J=8.3, 1.5 Hz, 1H, Ar—H), 7.57-7.54 (m, 2H, Ar—H), 7.47 (dd, J=8.3, 4.2 Hz, 1H, Ar—H), 4.32 (s, 2H, CH$_2$). $^{13}$C-NMR (100 MHz, CDCl$_3$): δ=164.6 (CO), 148.8 (CH), 138.8 (C$_q$), 136.6 (CH), 133.7 (C$_q$), 128.1 (C$_q$), 127.4 (CH), 122.7 (CH), 121.9 (CH), 116.9 (CH), 43.5 (CH$_2$). HRMS (ESI): m/z Calcd for $C_{11}H_9BrN_2O+H^+$ [M+H]$^+$ 264.9971 and 266.9953; Found 264.9966 and 266.9945.

Example 2: General Procedure for the Synthesis of ($^{R2}$NNN$^{8\text{-}Quin}$)-H Ligands

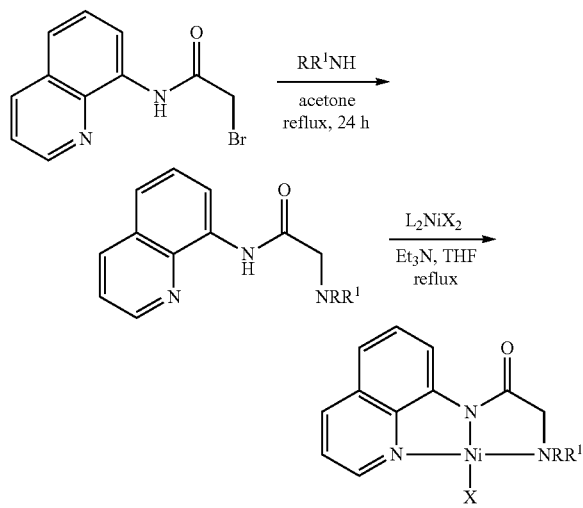

A mixture of 2-bromo-N-(quinolin-8-yl)acetamide (1.0 g, 3.77 mmol) and $Et_2NH$ (0.83 g, 11.35 mmol) in acetone (30 mL) was refluxed for 24 h. The reaction mixture was then cooled to room temperature and quenched with distilled $H_2O$ (20 mL). The crude aminated product was extracted with EtOAc (15 mL×3), and the combined organic extract was washed with $H_2O$ (15 mL×3) and dried over $Na_2SO_4$. After filtration and evaporation of the volatiles in vacuo, the crude product was purified by column chromatography on silica gel (n-hexane/EtOAc/Et$_3$N: 5/1/0.5) yielded the desired product ($^{Et2}$NNN$^{8\text{-}Quin}$)-H.

($^{Et2}$NNN$^{8\text{-}Quin}$)-H: Yield: 0.95 g, 98%. $^1$H-NMR (200 MHz, CDCl$_3$): δ=11.56 (br s, 1H, N—H), 8.85-8.79 (m, 2H, Ar—H), 8.12 (dd, J=8.3, 1.6 Hz, 1H, Ar—H), 7.57-7.46 (m, 2H, Ar—H), 7.41 (dd, J=8.3, 4.2 Hz, 1H, Ar—H), 3.29 (s, 2H, CH2), 2.70 (q, J=7.2 Hz, 4H, CH$_2$), 1.16 (t, J=7.2 Hz, 6H, CH$_3$). $^{13}$C-NMR (100 MHz, CDCl$_3$): δ=171.3 (CO), 148.6 (CH), 139.3 (C$_q$), 136.2 (CH), 134.7 (C$_q$), 128.2 (C$_q$), 127.4 (CH), 121.7 (CH), 121.6 (CH), 116.6 (CH), 59.2 (CH$_2$), 48.9 (2C, CH$_2$), 12.7 (2C, CH$_3$). ($^{Morph}$NNN$^{8\text{-}Quin}$)-H: Yield: 92%. $^1$H-NMR (400 MHz, CDCl$_3$): δ=11.45 (br s, 1H, N—H), 8.85 (dd, J=4.2, 1.6 Hz, 1H, Ar—H), 8.76 (dd, J=6.9, 1.8 Hz, 1H, Ar—H), 8.14 (dd, J=8.3, 1.6 Hz, 1H, Ar—H), 7.55-7.48 (m, 2H, Ar—H), 7.44 (dd, J=8.3, 4.3 Hz, 1H, Ar—H), 3.89 (t, J=4.5 Hz, 4H, CH$_2$), 3.27 (s, 2H, CH$_2$), 2.68 (t, J=4.5 Hz, 4H, CH$_2$). $^{13}$C-NMR (100 MHz, CDCl$_3$): δ=168.9 (CO), 148.7 (CH), 139.1 (C$_q$), 136.3 (CH), 134.4 (C$_q$), 128.2 (C$_q$), 127.4 (CH), 121.9 (CH), 121.7 (CH), 116.7 (CH), 67.4 (2C, CH$_2$), 62.9 (CH$_2$), 53.9 (2C, CH$_2$). ($^{Piper}$NNN$^{8\text{-}Quin}$)-H: $^1$H-NMR (400 MHz, CDCl$_3$): δ=11.43 (br s, 1H, N—H), 8.85 (dd, J=4.3, 1.8 Hz, 1H, Ar—H), 8.76 (dd, J=6.1, 2.8 Hz, 1H, Ar—H), 8.15 (dd, J=8.3, 1.8 Hz, 1H, Ar—H), 7.55-7.49 (m, 2H, Ar—H), 7.44 (dd, J=8.3, 4.3 Hz, 1H, Ar—H), 3.29 (s, 2H, CH$_2$), 2.73 (br s, 4H, CH$_2$), 2.64 (br s, 4H, CH$_2$), 2.38 (s, 3H, CH$_3$). $^{13}$C-NMR (100 MHz, CDCl$_3$): δ=169.3 (CO), 148.6 (CH), 139.2 (C$_q$), 136.3 (CH), 134.5 (C$_q$), 128.2 (C$_q$), 127.5 (CH), 121.8 (CH), 121.7 (CH), 116.7 (CH), 62.5 (CH$_2$), 55.5 (2C, CH$_2$), 53.5 (2C, CH$_2$), 46.2 (CH$_3$).

Example 3: Synthesis of ($^{Et2}$NNN$^{8\text{-}Quin}$)NiCl

To a schlenk flask equipped with magnetic stir bar was introduced ($^{Et2}$NNN$^{8\text{-}Quin}$)N—H (0.3 g, 1.166 mmol) and (DME)NiCl$_2$ (0.27 g, 1.229 mmol), and THF (20 mL) was added into it. Then, the Et$_3$N (0.16 mL, 1.148 mmol) was added and the reaction mixture was heated to reflux for 3 h. The reaction mixture was cooled to ambient temperature and all the volatiles were evaporated under vacuum. The resultant residue was washed with n-hexane (10 mL×3) and the product was extracted with toluene (10 mL×2). The toluene extract was concentrated and n-hexane was added to precipitate the pure product of ($^{Et2}$NNN$^{8\text{-}Quin}$)NiCl complex. Yield: 0.375 g, 92%. $^1$H-NMR (400 MHz, CDCl$_3$): δ=8.59 (d, J=7.9 Hz, 1H, Ar—H), 8.54 (dd, J=5.2, 0.9 Hz, 1H, Ar—H), 8.17 (dd, J=8.2, 1.2 Hz, 1H, Ar—H), 7.43 (vt, J=7.9 Hz, 1H, Ar—H), 7.29-7.25 (m, 2H, Ar—H), 3.20 (s, 2H, CH$_2$), 3.15 (app sextet, J=4.9 Hz, 2H, CH$_2$), 2.38 (t, J=7.0 Hz, 6H, CH$_3$), 2.06 (app sextet, J=5.5 Hz, 2H, CH$_2$). $^{13}$C-NMR (100 MHz, CDCl$_3$): δ=176.3 (CO), 151.4 (CH), 145.9 (C$_q$), 143.7 (C$_q$), 138.8 (CH), 129.4 (CH), 128.7 (C$_q$), 121.2 (CH), 119.6 (CH), 119.3 (CH), 63.5 (CH$_2$), 57.8 (2C, CH$_2$), 13.7 (2C, CH$_3$).

Example 4: Synthesis of ($^{Et2}$NNN$^{8\text{-}Quin}$)Ni(OAc)

This complex was synthesized following the procedure similar to the synthesis of ($^{Et2}$NNN$^{8\text{-}Quin}$)NiCl, using (^{Et2}NNN^{8-Quin})N—H (0.3 g, 1.166 mmol), Ni(OAc)$_2$ (0.216 g, 1.222 mmol) and Et$_3$N (0.16 mL, 1.148 mmol).

$^1$H-NMR (400 MHz, CDCl$_3$): δ=8.46 (d, J=7.5 Hz, 1H, Ar—H), 8.19 (d, J=7.8 Hz, 1H, Ar—H), 7.55 (d, J=4.5 Hz, 1H, Ar—H), 7.42 (vt, J=7.9 Hz, 1H, Ar—H), 7.32-7.22 (m, 2H, Ar—H), 3.22 (s, 2H, CH$_2$), 2.86 (app sextet, J=5.1 Hz, 2H, CH$_2$), 2.34 (t, J=6.7 Hz, 6H, CH$_3$), 2.21 (app sextet, J=6.1 Hz, 2H, CH$_2$), 1.98 (s, 3H, CH$_3$). $^{13}$C-NMR (100 MHz, CDCl$_3$): δ=178.6 (CO), 175.2 (CO), 148.7 (CH), 145.6 (C$_q$), 143.4 (C$_q$), 138.7 (CH), 129.4 (CH), 128.8 (C$_q$), 121.4 (CH), 119.7 (CH), 119.0 (CH), 62.6 (CH$_2$), 56.1 (2C, CH$_2$), 24.5 (COCH$_3$), 13.1 (2C, CH$_3$).

Example 5: Representative Procedure for the Alkylation of Indoles:

a) Synthesis of 2-Octyl-1-(Pyridine-2-yl)-1H-Indole:

To a flame-dried screw-capped tube equipped with a magnetic stir bar were introduced 1-pyridine-2-yl-1H-indole (0.58 g, 0.3 mmol), 1-iodooctane (0.144 g, 0.6 mmol), ($^{Et2}$NNN$^{8-Quin}$)Ni(OAc) (0.0056 g, 0.015 mmol, 5.0 mol %), LiHMDS (0.010 g, 0.06 mmol, 20 mol %) and LiOtBu (0.048 g, 0.60 mmol), and toluene (0.15 mL) was added into it. The resultant reaction mixture was stirred at 150° C. in a preheated oil bath for 16 h. At ambient temperature, H$_2$O (5 mL) was added and the reaction mixture was extracted with CH$_2$Cl$_2$ (20 mL×3). The combined organic layers were dried over Na$_2$SO$_4$ and the solvent was evaporated in vacuo. The remaining residue was purified using column chromatography on neutral alumina (n-hexane—EtOAc 50/1) to yield desired compound (0.075 g, 82%) as an oily liquid. $^1$H-NMR (500 MHz, CDCl$_3$): δ=8.68 (d, J=5.0 Hz, 1H, Ar—H), 7.88 (td, J=7.6, 1.8 Hz, 1H, Ar—H), 7.60-7.58 (m, 1H, Ar—H), 7.44 (d, J=8.0 Hz, 1H, Ar—H), 7.35-7.31 (m, 2H, Ar—H), 7.16-7.12 (m, 2H, Ar—H), 6.47 (s, 1H, Ar—H), 2.85 (t, J=7.6 Hz, 2H, CH$_2$), 1.61-1.55 (m, 2H, CH$_2$), 1.31-1.24 (m, 10H, CH$_2$), 0.89 (t, J=6.9 Hz, 3H, CH$_3$). $^{13}$C{$^1$H}-NMR (125 MHz, CDCl$_3$): δ=151.8 (C$_q$), 149.8 (CH), 141.9 (C$_q$), 138.4 (CH), 137.4 (C$_q$), 128.8 (C$_q$), 122.1 (CH), 121.7 (CH), 121.3 (CH), 120.7 (CH), 120.0 (CH), 110.2 (CH), 102.2 (CH), 32.0 (CH$_2$), 29.5 (2C, CH$_2$), 29.3 (CH$_2$), 28.7 (CH$_2$), 27.6 (CH$_2$), 22.8 (CH$_2$), 14.3 (CH$_3$). HRMS (ESI): m/z Calcd for C$_{21}$H$_{26}$N$_2$+H$^+$ [M+H]$^+$ 307.2169; Found 307.2172.

b) 2-Octadecyl-1-(Pyridin-2-yl)-1H-Indole (5aj):

The representative procedure was followed, using substrate 3a (0.058 g, 0.3 mmol), 1-bromooctadecane (4j; 0.20 g, 0.6 mmol) and KI (0.1 g, 0.6 mmol), and the reaction mixture was stirred for 20 h. Purification by column chromatography on neutral alumina (Pet ether/EtOAc/Et3N: 50/1/0.5) yielded 5aj (0.075 g, 56%) as a light yellow solid. $^1$H-NMR (400 MHz, CDCl$_3$): 45=8.68 (dd, J=5.0, 1.8 Hz, 1H, Ar—H), 7.92-7.87 (m, 1H, Ar—H), 7.61-7.57 (m, 1H, Ar—H), 7.44 (d, J=8.2 Hz, 1H, Ar—H), 7.35-7.32 (m, 2H, Ar—H), 7.15-7.12 (m, 2H, Ar—H), 6.46 (s, 1H, Ar—H), 2.85 (t, J=7.3 Hz, 2H, CH$_2$), 1.60-1.58 (m, 2H, CH$_2$), 1.36-1.24 (m, 30H, CH$_2$), 0.91 (t, J=6.4 Hz, 3H, CH$_3$). $^{13}$C{$^1$H}-NMR (100 MHz, CDCl$_3$): δ=151.8 (C$_q$), 149.8 (CH), 142.0 (C$_q$), 138.4 (CH), 137.4 (C$_q$), 128.8 (C$_q$), 122.2 (CH), 121.7 (CH), 121.3 (CH), 120.7 (CH), 120.0 (CH), 110.2 (CH), 102.2 (CH), 32.1 (CH$_2$), 29.9 (8C, CH$_2$), 29.8 (CH$_2$), 29.7 (CH$_2$), 29.6 (2C, CH$_2$), 29.5 (2C, CH$_2$), 28.8 (CH$_2$), 27.6 (CH$_2$), 22.9 (CH$_2$), 14.3 (CH$_3$). HRMS (ESI) m/z Calcd for C$_{31}$H$_{46}$N$_2$+H$^+$ [M+H]$^+$ 447.3734; Found 447.3730.

c) 2-Dodecyl-5-Methyl-1-(Pyridin-2-yl)-1H-Indole (5bf):

The representative procedure was followed using, 5-methyl-1-(pyridine-2-yl)-1H-indole (3b; 0.062 g, 0.3 mmol) and iodide 4f (0.178 g, 0.6 mmol), and the reaction mixture was stirred for 16 h. Purification by column chromatography on neutral alumina (Pet ether/EtOAc/Et3N: 20/1/0.5) yielded 5bf (0.105 g, 93%) a light yellow liquid. $^1$H-NMR (500 MHz, CDCl$_3$): δ=8.67 (dd, J=5.0, 1.5 Hz, 1H, Ar—H), 7.87 (td, J=7.6, 1.9 Hz, 1H, Ar—H), 7.42 (d, J=8.0 Hz, 1H, Ar—H), 7.37 (s, 1H, Ar—H), 7.31-29 (m, 1H, Ar—H), 7.24 (d, J=8.4 Hz, 1H, Ar—H), 6.96 (dd, J=8.3, 1.1 Hz, 1H, Ar—H), 6.38 (s, 1H, Ar—H), 2.84 (t, J=7.6 Hz, 2H, CH$_2$), 2.45 (s, 3H, CH$_3$), 1.59-1.53 (m, 2H, CH$_2$), 1.34-1.23 (m, 18H, CH$_2$), 0.91 (t, J=6.9 Hz, 3H, CH$_3$). $^{13}$C{$^1$H}-NMR (125 MHz, CDCl$_3$): 152.0 (C$_q$), 149.7 (CH), 142.0 (C$_q$), 138.3 (CH), 135.8 (C$_q$), 129.9 (C$_q$), 129.1 (C$_q$), 123.1 (CH), 121.9 (CH), 121.1 (CH), 119.8 (CH), 109.9 (CH), 101.9 (CH), 32.1 (CH$_2$), 29.8 (CH$_2$), 29.8 (CH$_2$), 29.8 (CH$_2$), 29.7 (CH$_2$), 29.5 (2C, CH$_2$), 29.5 (CH$_2$), 28.8 (CH$_2$), 27.7 (CH$_2$), 22.9 (CH$_2$), 21.5 (CH$_3$), 14.3 (CH$_3$). HRMS (ESI): m/z Calcd for C$_{26}$H$_{36}$N$_2$+H$^+$ [M+H]$^+$ 377.2946; Found 377.2951.

d) 5-Methoxy-2-Octyl-1-(Pyridin-2-yl)-1H-Indole (5ca):

The representative procedure was followed, using 5-methoxy-1-(pyridine-2-yl)-1H-indole (3c; 0.067 g, 0.3 mmol) and iodide 4a (0.144 g, 0.6 mmol), and the reaction mixture was stirred for 16 h. Purification by column chromatography on neutral alumina (Pet ether/EtOAc/Et3N: 10/1/0.5) yielded 5ca (0.053 g, 53%) as a light yellow liquid. $^1$H-NMR (400 MHz, CDCl$_3$): δ=8.63 (dd, J=4.4, 1.0 Hz, 1H, Ar—H), 7.85 (td, J=7.8, 1.8 Hz, 1H, Ar—H), 7.38 (d, J=8.3 Hz, 1H, Ar—H), 7.29-26 (m, 1H, Ar—H), 7.22 (d, J=8.8 Hz, 1H, Ar—H), 7.04 (d, J=2.5 Hz, 1H, Ar—H), 6.76 (dd, J=8.8, 2.5 Hz, 1H, Ar—H), 6.36 (s, 1H, Ar—H), 3.84 (s, 3H, CH$_3$), 2.81 (t, J=7.3 Hz, 2H, CH$_2$), 1.58-1.50 (m, 2H, CH$_2$), 1.31-1.21 (m, 10H, CH$_2$), 0.86 (t, J=6.6 Hz, 3H, CH$_3$). $^{13}$C{$^1$H}-NMR (100 MHz, CDCl$_3$): 154.9 (C$_q$), 151.9 (C$_q$), 149.7 (CH), 142.6 (C$_q$), 138.4 (CH), 132.6 (C$_q$), 129.4 (C$_q$), 121.9 (CH), 121.0 (CH), 111.2 (CH), 111.0 (CH), 102.3 (CH), 102.1 (CH), 56.0 (CH$_3$), 32.0 (CH$_2$), 29.5 (2C, CH$_2$), 29.3 (CH$_2$), 28.8 (CH$_2$), 27.7 (CH$_2$), 22.8 (CH$_2$), 14.3 (CH$_3$). HRMS (ESI): m/z Calcd for C$_{22}$H$_{28}$N$_2$O+H$^+$ [M+H]$^+$ 337.2274; Found 337.2273. The $^1$H and $^{13}$C spectra are consistent with those reported in the literature.[4]

e) 2-Octyl-1-(Pyridin-2-yl)-1H-Indole-5-Carbonitrile (5fa):

The representative procedure was followed using, 1-(pyridin-2-yl)-1H-indole-5-carbonitrile (3f; 0.066 g, 0.3 mmol) and iodide 4a (0.144 g, 0.6 mmol), and the reaction mixture was stirred for 16 h. Purification by column chromatography on neutral alumina (Pet ether/EtOAc/Et3N: 20/1/0.5) yielded 5fa (0.038 g, 38%) a light yellow liquid. $^1$H-NMR (400 MHz, CDCl$_3$): δ=8.69 (dd, J=4.4, 1.0 Hz, 1H, Ar—H), 7.95 (td, J=7.8, 2.0 Hz, 1H, Ar—H), 7.90 (s, 1H, Ar—H), 7.43-7.39 (m, 2H, Ar—H), 7.36-7.29 (m, 2H, Ar—H), 6.50 (s, 1H, Ar—H), 2.78 (t, J=7.3 Hz, 2H, CH$_2$), 1.56 (pent, J=7.3 Hz, 2H, CH$_2$), 1.30-1.22 (m, 10H, CH$_2$), 0.86 (t, J=6.9 Hz, 3H, CH$_3$). $^{13}$C{$^1$H}-NMR (100 MHz, CDCl$_3$): 150.7 (CN), 150.2 (CH), 144.6 (C$_q$), 139.1 (C$_q$), 138.8 (CH), 128.6 (C$_q$), 125.3 (CH), 124.9 (CH), 123.2 (CH), 121.6 (CH), 120.9 (C$_q$), 111.1 (CH), 103.7 (C$_q$), 102.4 (CH), 32.0 (CH$_2$), 29.4 (2C, CH$_2$), 29.3 (CH$_2$), 28.5 (CH$_2$), 27.5 (CH$_2$), 22.8 (CH$_2$), 14.3 (CH$_3$). HRMS (ESI): m/z Calcd for C$_{22}$H$_{25}$N$_3$+H$^+$ [M+H]$^+$ 332.2121; Found 332.2119.

f) 2-Dodecyl-1-(Pyridin-2-yl)-1H-Indole-5-Carbonitrile (5ff):

The representative procedure was followed using, substrate 3f (0.066 g, 0.3 mmol) and iodide 4f (0.178 g, 0.6 mmol), and the reaction mixture was stirred for 16 h. Purification by column chromatography on neutral alumina (Pet ether/EtOAc/Et3N: 20/1/0.5) yielded 5ff (0.052 g, 45%) a light yellow liquid. $^1$H-NMR (500 MHz, CDCl$_3$): δ=8.69 (d, J=4.2 Hz, 1H, Ar—H), 7.94 (td, J=7.6, 1.5 Hz, 1H, Ar—H), 7.89 (s, 1H, Ar—H), 7.42-7.38 (m, 2H, Ar—H), 7.34-7.29 (m, 2H, Ar—H), 6.49 (s, 1H, Ar—H), 2.78 (t, J=7.6 Hz, 2H, CH$_2$), 1.56 (pent, J=7.4 Hz, 2H, CH$_2$), 1.34-1.22 (m, 18H, CH$_2$), 0.88 (t, J=6.9 Hz, 3H, CH$_3$). $^{13}$C{$^1$H}-NMR (125 MHz, CDCl$_3$): 150.7 (CN), 150.1 (CH), 144.6 (C$_q$), 139.1 (C$_q$), 138.8 (CH), 128.6 (C$_q$), 125.2 (CH), 124.8 (CH), 123.2 (CH), 121.5 (CH), 120.9 (C$_q$), 111.1 (CH), 103.7 (C$_q$), 102.3 (CH), 32.1 (CH$_2$), 29.8 (CH$_2$), 29.8 (CH$_2$), 29.7 (CH$_2$), 29.6 (CH$_2$), 29.5 (CH$_2$), 29.4 (CH$_2$), 29.4 (CH$_2$), 28.5 (CH$_2$), 27.5 (CH$_2$), 22.8 (CH$_2$), 14.3 (CH$_3$). HRMS (ESI): m/z Calcd for C$_{26}$H$_{33}$N$_3$+H$^+$ [M+H]$^+$ 388.2747; Found 388.2744.

g) 1-(Pyrimidin-2-yl)-2-Tetradecyl-1H-Indole (5hh):

The representative procedure was followed, using 1-(pyrimidin-2-yl)-1H-indole (3h; 0.039 g, 0.2 mmol), bromide 4h (0.111 g, 0.4 mmol) and KI (0.067 g, 0.4 mmol), and the reaction mixture was stirred for 24 h. Purification by column chromatography on neutral alumina (Pet ether/EtOAc/Et3N: 50/1/0.5) yielded 5hh (0.044 g, 56%) as a light yellow liquid. $^1$H-NMR (500 MHz, CDCl$_3$): δ=8.80 (d, J=5.0 Hz, 2H, Ar—H), 8.21 (d, J=8.0 Hz, 1H, Ar—H), 7.53 (d, J=7.2 Hz, 1H, Ar—H), 7.22-7.14 (m, 3H, Ar—H), 6.47 (s, 1H, Ar—H), 3.15 (t, J=7.8 Hz, 2H, CH$_2$), 1.61 (pent, J=7.6 Hz, 2H, CH$_2$), 1.39-1.33 (m, 2H, CH$_2$), 1.31-1.22 (m, 20H, CH$_2$), 0.88 (t, J=6.9 Hz, 3H, CH$_3$). $^{13}$C{$^1$H}-NMR (125 MHz, CDCl$_3$): 158.5 (C$_q$), 158.3 (2C, CH), 142.6 (C$_q$), 137.1 (C$_q$), 129.6 (C$_q$), 122.5 (CH), 121.9 (CH), 119.8 (CH), 117.2 (CH), 113.7 (CH), 105.6 (CH), 32.1 (CH$_2$), 29.9 (3C, CH$_2$), 29.8 (2C, CH$_2$), 29.8 (CH$_2$), 29.7 (2C, CH$_2$), 29.6 (CH$_2$), 29.5 (CH$_2$), 29.2 (CH$_2$), 22.9 (CH$_2$), 14.3 (CH$_3$). HRMS (ESI): m/z Calcd for C$_{26}$H$_{37}$N$_3$+H$^+$ [M+H]$^+$ 392.3060; Found 392.3053.

h) 2-Benzyl-1-(Pyridin-2-yl)-1H-Indole:

$^1$H-NMR (500 MHz, CDCl$_3$): δ=8.66 (dd, J=3.8, 0.8 Hz, 1H, Ar—H), 7.77 (td, J=8.0, 1.7 Hz, 1H, Ar—H), 7.62-7.56 (m, 1H, Ar—H), 7.36-7.31 (m, 1H, Ar—H), 7.29-7.26 (m, 2H, Ar—H), 7.20-7.13 (m, 5H, Ar—H), 7.06 (d, J=6.9 Hz, 2H, Ar—H), 6.40 (s, 1H, Ar—H), 4.28 (s, 2H, CH2). $^{13}$C{$^1$H}-NMR (125 MHz, CDCl$_3$): 151.5 (C$_q$), 149.7 (CH), 140.3 (C$_q$), 138.9 (C$_q$), 138.3 (CH), 137.6 (C$_q$), 129.0 (2C, CH), 128.6 (C$_q$), 128.3 (2C, CH), 126.3 (CH), 122.2 (CH), 122.0 (CH), 121.3 (CH), 120.8 (CH), 120.3 (CH), 110.2 (CH), 104.3 (CH), 34.2 (CH2). HRMS (ESI): m/z Calcd for C$_{20}$H$_{16}$N$_2$+H$^+$ [M+H]$^+$ 285.1386; Found 285.1386.

Example 6: Representative Procedure for Benzylation of Indoles a) Synthesis of 2-Benzyl-1-(Pyridin-2-yl)-1H-Indole (7aa):

Procedure A: To a flame dried screw-cap tube (5 mL) equipped with magnetic stir bar was introduced 1-pyridine-2-yl-1H-indole (3a; 0.058 g, 0.3 mmol), 2-iodobutane (0.083 g, 0.45 mmol), cat 1a (0.0056 g, 0.015 mmol, 5.0 mol %), LiHMDS (0.010 g, 0.06 mmol, 20 mol %), LiO$^t$Bu (0.048 g, 0.6 mmol) and toluene (6a; 0.96 mL, 9.0 mmol) inside the glove-box. The resultant reaction mixture was stirred at 150° C. in a preheated oil bath for 20 h. At ambient temperature, the reaction mixture was quenched with distilled H$_2$O (10 mL) and then neutralized with 2N HCl (0.5 mL). The crude product was then extracted with CH$_2$Cl$_2$ (20 mL×3). The combined organic extract was dried over Na$_2$SO$_4$ and the volatiles were evaporated in vacuo. The remaining residue was purified by column chromatography on neutral alumina (petroleum ether/EtOAc/Et$_3$N: 20/1/0.5) to yield 7aa (0.060 g, 70%) as a light yellow liquid.

Procedure B: This procedure was similar to procedure A, except the solvent chlorobenzene (0.304 mL, 3.0 mmol, 10 equiv) was added in addition to toluene (0.96 mL, 9.0 mmol, 30 equiv). The yield of the product 7aa obtained by this procedure was 82% (0.070 g).

2-Benzyl-1-(pyridin-2-yl)-1H-indole (7aa): $^1$H-NMR (500 MHz, CDCl$_3$): δ=8.66 (dd, J=3.8, 0.8 Hz, 1H, Ar—H), 7.77 (td, J=8.0, 1.7 Hz, 1H, Ar—H), 7.62-7.56 (m, 1H, Ar—H), 7.36-7.31 (m, 1H, Ar—H), 7.29-7.26 (m, 2H, Ar—H), 7.20-7.13 (m, 5H, Ar—H), 7.06 (d, J=6.9 Hz, 2H, Ar—H), 6.40 (s, 1H, Ar—H), 4.28 (s, 2H, CH$_2$). $^{13}$C{$^1$H}-NMR (125 MHz, CDCl$_3$): δ=151.5 (C$_q$), 149.7 (CH), 140.3 (C$_q$), 138.9 (C$_q$), 138.3 (CH), 137.6 (C$_q$), 129.0 (2C, CH), 128.6 (C$_q$), 128.3 (2C, CH), 126.3 (CH), 122.2 (CH), 122.0 (CH), 121.3 (CH), 120.8 (CH), 120.3 (CH), 110.2 (CH), 104.3 (CH), 34.2 (CH$_2$). HRMS (ESI): m/z Calcd for C$_{20}$H$_{16}$N$_2$+H$^+$ [M+H]$^+$ 285.1386; Found 285.1386.

b) 2-(4-Methylbenzyl)-1-(Pyridin-2-yl)-1H-Indole (7ab):

The representative procedure A was followed, using substrate 3a (0.058 g, 0.3 mmol) and p-xylene (6b; 1.1 mL, 9.0 mmol). Purification by column chromatography on neutral alumina (petroleum ether/EtOAc/Et$_3$N: 30/1/0.5) yielded 7ab (0.074 g, 83%) as a light yellow liquid. $^1$H-NMR (500 MHz, CDCl$_3$): δ=8.68 (d, J=4.2 Hz, 1H, Ar—H), 7.78 (td, J=8.0, 1.3 Hz, 1H, Ar—H), 7.60 (dd, J=5.7, 3.1 Hz, 1H, Ar—H), 7.37-7.35 (m, 1H, Ar—H), 7.32-7.28 (m, 2H, Ar—H), 7.19-7.16 (m, 2H, Ar—H), 7.03 (d, J=8.0 Hz, 2H, Ar—H), 6.99 (d, J=7.9 Hz, 2H, Ar—H), 6.40 (s, 1H, Ar—H), 4.25 (s, 2H, CH$_2$), 2.32 (s, 3H, CH$_3$). $^{13}$C{$^1$H}-NMR (125 MHz, CDCl$_3$): δ=151.5 (C$_q$), 149.6 (CH), 140.6 (C$_q$), 138.3 (CH), 137.6 (C$_q$), 135.8 (C$_q$), 135.7 (C$_q$), 129.0 (2C, CH), 128.9 (2C, CH), 128.6 (C$_q$), 122.1 (CH), 121.9 (CH), 121.3 (CH), 120.8 (CH), 120.3 (CH), 110.2 (CH), 104.1 (CH), 33.7 (CH$_2$), 21.1 (CH$_3$). HRMS (ESI): m/z Calcd for C$_{21}$H$_{18}$N$_2$+H$^+$ [M+H]$^+$ 299.1543; Found 299.1542.

c) 2-(4-Methoxybenzyl)-1-(Pyridin-2-yl)-1H-Indole (7ac):

The representative procedure B was followed, using substrate 3a (0.058 g, 0.3 mmol) and 1-methoxy-4-methylbenzene (6c; 1.13 mL, 9.0 mmol). Purification by column chromatography on neutral alumina (petroleum ether/EtOAc/Et$_3$N: 10/1/0.5) yielded 7ac (0.062 g, 66%) as a light yellow liquid. $^1$H-NMR (500 MHz, CDCl$_3$): δ=8.65 (dd, J=4.6, 0.8 Hz, 1H, Ar—H), 7.77 (td, J=7.6, 1.9 Hz, 1H, Ar—H), 7.57 (dd, J=5.7, 3.1 Hz, 1H, Ar—H), 7.32 (dd, J=5.7, 3.1 Hz, 1H, Ar—H), 7.29-7.25 (m, 2H, Ar—H), 7.15-7.12 (m, 2H, Ar—H), 6.97 (d, J=8.8 Hz, 2H, Ar—H), 6.73 (d, J=8.8 Hz, 2H, Ar—H), 6.37 (s, 1H, Ar—H), 4.19 (s, 2H, CH$_2$), 3.75 (s, 3H, CH$_3$). $^{13}$C{$^1$H}-NMR (125 MHz, CDCl$_3$): δ=158.1 (C$_q$), 151.5 (C$_q$), 149.6 (CH), 140.8 (C$_q$), 138.3 (CH), 137.6 (C$_q$), 130.9 (C$_q$), 130.0 (2C, CH), 128.6 (C$_q$), 122.2 (CH), 122.0 (CH), 121.4 (CH), 120.8 (CH), 120.3 (CH), 113.8 (2C, CH), 110.2 (CH), 104.1 (CH), 55.4 (CH$_2$), 33.3 (CH$_3$). HRMS (ESI): m/z Calcd for C$_{21}$H$_{18}$N$_2$O+H$^+$ [M+H]$^+$ 315.1492; Found 315.1489.

d) 2-(4-Fluorobenzyl)-1-(Pyridin-2-yl)-1H-Indole (7ad):

The representative procedure A was followed, using substrate 2a (0.058 g, 0.3 mmol) and 1-fluoro-4-methylbenzene (6d; 0.99 mL, 9.0 mmol). Purification by column chromatography on neutral alumina (petroleum ether/EtOAc/Et$_3$N: 20/1/0.5) yielded 7ad (0.069 g, 76%) as a light yellow liquid. $^1$H-NMR (500 MHz, CDCl$_3$): δ=8.64 (dd, J=5.7, 1.9 Hz, 1H, Ar—H), 7.77 (td, J=7.6, 1.9 Hz, 1H, Ar—H), 7.59 (dd, J=5.7, 3.1 Hz, 1H, Ar—H), 7.33-7.30 (m, 1H, Ar—H), 7.28-7.26 (m, 2H, Ar—H), 7.17-7.14 (m, 2H, Ar—H), 7.00-6.97 (m, 2H, Ar—H), 6.89-6.80 (m, 2H, Ar—H), 6.39 (s, 1H, Ar—H), 4.24 (s, 2H, CH$_2$). $^{13}$C{$^1$H}-NMR (125 MHz, CDCl$_3$): δ=161.5 (d, $^1J_{C-F}$=244.1 Hz, C$_q$), 151.4 (C$_q$), 149.7 (CH), 140.2 (C$_q$), 138.4 (CH), 137.6 (C$_q$), 134.6 (d, $^4J_{C-F}$=2.9 Hz, C$_q$), 130.4 (d, $^3J_{C-F}$=7.6 Hz, 2C, CH), 128.5 (C$_q$), 122.2 (CH), 122.2 (CH), 121.3 (CH), 120.9 (CH), 120.4 (CH), 115.1 (d, $^2J_{C-F}$=21.0 Hz, 2C, CH), 110.2 (CH), 104.3 (CH), 33.4 (CH$_2$). $^{19}$F-NMR (377 MHz, CDCl$_3$): δ=−117.0 (s). HRMS (ESI): m/z Calcd for C$_{20}$H$_{15}$FN$_2$+H$^+$ [M+H]$^+$ 303.1292; Found 303.1293.

Advantages of Invention

1. Novel and inexpensive nickel catalysts of formula (I) is provided.
2. Novel compounds of formula (II) provided.
3. The Novel and inexpensive nickel catalysts effectively used to performs the alkylation and benzylation indoles, pyrazoles, imidazoles, etc.

The invention claimed is:

1. A nickel catalyst of formula (I):

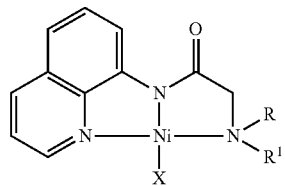

Formula I wherein:
R and R$^1$ are the same and are selected from the group consisting of alkyl, aryl, benzyl, heteroaryl; and
X is selected from the group consisting of hydrogen, halogen, OC(O)CH$_3$, OC(O)$^t$Bu, OC(O)Ph, OC(O)admantyl, OSO$_2$CF$_3$, BF$_4$, and SbF$_6$.

2. The nickel catalyst of claim 1, wherein said nickel catalyst of formula (I) is selected from the group consisting of:
a nickel catalyst of formula (I), wherein R and R$^1$ are ethyl and X is chloro; and
a nickel catalyst of formula (I), wherein R and R$^1$ are ethyl and X is OC(O)CH$_3$.

3. A process for the preparation of the nickel catalyst of formula (I) of claim 1, the process comprising:
(a) refluxing a reaction mixture of 2-bromo-N-(quinolin-8-yl) acetamide and an amino compound in a solvent for from 20 hours to 24 hours at a temperature from 60° C. to 80° C., to afford a ligand having formula (IA):

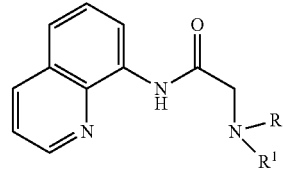

(IA)

where R and R$^1$ are the same as in the nickel catalyst of formula (I); and
(b) adding triethylamine to a mixture of the ligand afforded in (a), a nickel compound, and a solvent, followed by refluxing the resulting reaction mixture for 3 hours to 12 hours at a temperature from 60° C. to 70° C., to afford the nickel catalyst of formula (I).

4. The process of claim 3, wherein said amino compound is selected from diisopropyl amine, diethylamine, and dimethyl amine; and wherein said nickel compound is selected from (DME)NiCl$_2$, (THF)NiBr$_2$, and Ni(OAc)$_2$, where DME is dimethoxyethane, THF is tetrahydrofuran, and OAc is acetate.

5. The process of claim 3, wherein said solvent in (a) and (b) is selected from acetone or tetrahydrofuran (THF).

6. A process for the alkylation or benzylation of a heteroarene using a nickel catalyst according to claim 1, the process comprising:
stirring a reaction mixture of (a)-(e):
(a) the heteroarene,
(b) an organic halide compound or a benzyl compound,
(c) the nickel catalyst of formula (I),
(d) a base, and
(e) a solvent,
at a temperature from 120° C. to 160° C. for a period of 6 hours to 36 hours, to afford either:
an alkylated heteroarene compound when (b) is the organic halide compound; or
a benzylated heteroarene compound when (b) is the benzyl compound,
wherein:
the heteroarene has formula (3):

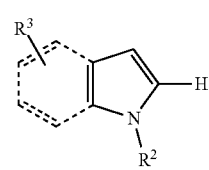

(3)

where:
R$^2$ is 2-pyridine, 2-pyrimidine, 2,4-pyrazine, or 2-oxazole; and
each R$^3$ is hydrogen, alkyl, alkoxy, substituted alkoxy, phenoxy, halogen, or trifluoromethyl;

the organic halide compound has formula X—R$^4$, where X is chlorine, bromine, or iodine and R$^4$ is alkyl, whereby the alkylated heteroarene compound has formula (II):

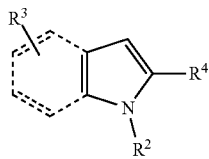

(II)

where R$^2$ and each R$^3$ are the same as in formula (3), and where R$^4$ is the same as in the organic halide compound; and the benzyl compound has formula (6):

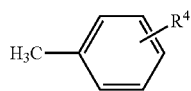

(6)

where R$^4$ is hydrogen, methyl, or alkoxy, whereby the benzylated heteroarene compound has formula (III):

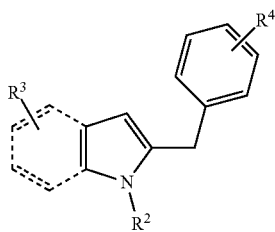

(III)

where R$^2$ and R$^3$ are the same as in formula (3) and R$^4$ is the same as in formula (6).

7. The process of claim 6, wherein said heteroarene is selected from the group consisting of 1-(pyridine-2-yl)-1H-indole, 5-methyl-1-(pyridine-2-yl)-1H-indole, 5-methoxy-1-(pyridine-2-yl)-1H-indole, 5-fluoro-1-(pyridine-2-yl)-1H-indole, 5-bromo-1-(pyridine-2-yl)-1H-indole, 1-(pyridin-2-yl)-1H-indole-5-carbonitrile, 3-methyl-1-(pyridine-2-yl)-1H-indole, 1-(pyrimidin-2-yl)-1H-indole, and 5-methoxy-1-(pyrimidin-2-yl)-1H-indole.

8. The process of claim 6, wherein said organic halide compound is selected from the group consisting of 1-iodobutane, 1-iodopentane, 1-bromohexane, 1-bromodecane, 1-iodododecane, 1-bromotridecane, 1-bromotetradecane, 1-bromohexadecane, 1-bromooctadecane, 1-bromo-2-methylpropane, 1-bromo-3-methylbutane, (bromomethyl)cyclohexane, (2-bromoethyl)cyclohexane, 1-bromo-2,2-dimethylpropane, (3-bromopropyl)benzene, 1-(3-bromopropyl)-4-methoxybenzene, 1-chloro-4-iodobutane, 5-bromopent-1-ene, 9-(4-iodobutyl)-8a,9a-dihydro-9H-carbazole, 2-iodopropane, (1-bromoethyl)benzene, (bromoethylene)dibenzene, 2-iodobutane, bromocyclopropane, iodocyclopentane, bromocyclohexane, bromocycloheptane, and 6-bromo-1-hexene.

9. The process of claim 6, wherein said benzyl compound is selected from the group consisting of toluene, p-xylene, m-xylene, 1-methoxy-4-methylbenzene, 1-fluoro-4-methylbenzene, 1-chloro-4-methylbenzene, 1-bromo-4-methylbenzene, ortho-xylene, 1-fluoro-2-methylbenzene, 1-chloro-2-methylbenzene, 1-bromo-2-methylbenzene, 1-methyl-2-(trifluoromethyl)benzene, mesitylene, 2,4-difluoro-1-methylbenzene, 1-methylnaphthalene, and 1-(p-tolyl)-1H-indoletoluene.

10. The process of claim 6, wherein said base is selected from lithium bis(trimethylsilyl)amide, lithium tert-butoxide, or mixture thereof; and wherein said solvent is selected from toluene, chlorobenzene, or mixture thereof.

* * * * *